(12) United States Patent
Leeflang et al.

(10) Patent No.: US 9,271,631 B2
(45) Date of Patent: Mar. 1, 2016

(54) ORAL AIRWAY DEVICES AND METHODS FOR MAKING AND USING THEM

(76) Inventors: Stephen A. Leeflang, Sunnyvale, CA (US); Christian S. Eversull, Palo Alto, CA (US)

(*) Notice: Subject to any disclaimer, the term of this patent is extended or adjusted under 35 U.S.C. 154(b) by 451 days.

(21) Appl. No.: 13/419,430

(22) Filed: Mar. 13, 2012

(65) Prior Publication Data

US 2012/0283513 A1 Nov. 8, 2012

Related U.S. Application Data

(60) Provisional application No. 61/452,116, filed on Mar. 13, 2011, provisional application No. 61/559,244, filed on Nov. 14, 2011.

(51) Int. Cl.
*A61M 16/00* (2006.01)
*A61B 1/00* (2006.01)
*A61B 1/015* (2006.01)
*A61B 1/24* (2006.01)

(52) U.S. Cl.
CPC .......... *A61B 1/00071* (2013.01); *A61B 1/00154* (2013.01); *A61B 1/015* (2013.01); *A61B 1/24* (2013.01)

(58) Field of Classification Search
CPC ....... A61B 1/24; A61B 1/00071; A61B 1/267
USPC .............................. 600/185–200; 128/200.26
See application file for complete search history.

(56) References Cited

U.S. PATENT DOCUMENTS

| | | | |
|---|---|---|---|
| 2,705,959 A | 4/1955 | Elmore | |
| 3,756,244 A | 9/1973 | Kinnear et al. | |
| 4,640,273 A | 2/1987 | Greene et al. | |
| 4,683,879 A * | 8/1987 | Williams | 128/200.26 |
| 5,024,218 A | 6/1991 | Ovassapian et al. | |
| 5,273,032 A | 12/1993 | Borody | |
| 5,937,858 A | 8/1999 | Connell | |
| 6,098,617 A * | 8/2000 | Connell | 128/200.26 |
| 6,568,388 B2 | 5/2003 | Christopher | |
| 7,036,501 B2 | 5/2006 | Wall | |
| 7,171,962 B1 | 2/2007 | Bloem | |
| 7,182,728 B2 * | 2/2007 | Cubb et al. | 600/194 |
| 7,278,420 B2 | 10/2007 | Ganesh et al. | |
| 7,624,736 B2 | 12/2009 | Borody | |
| 8,529,442 B2 * | 9/2013 | Pacey et al. | 600/188 |
| 2004/0129272 A1 * | 7/2004 | Ganesh et al. | 128/207.14 |
| 2008/0000481 A1 * | 1/2008 | Ganesh et al. | 128/207.14 |
| 2009/0013995 A1 * | 1/2009 | Williams | 128/200.26 |

* cited by examiner

*Primary Examiner* — Kevin T Truong
*Assistant Examiner* — Si Ming Ku
(74) *Attorney, Agent, or Firm* — William A. English; Vista IP Law Group LLP

(57) ABSTRACT

Airway devices are provided for introducing an endoscope into a patient's gastrointestinal system that include a tubular proximal portion sized for placement in an oral cavity and including a passage for receiving an endoscope therethrough, and a curved distal portion. The distal portion may have a "C" shaped wall defining a channel extending from the passage to a distal tip of the distal portion. The proximal portion may include a flange for placement adjacent the patient's teeth when the airway device is inserted into the oral cavity, and the airway device may include sampling and fluid delivery lumens including ports on the face of the flange. The sampling lumen may include an inlet port within the passage, and the fluid delivery lumen may include an outlet port communicating with the channel such that the outlet port is offset distally relative to the inlet port.

15 Claims, 14 Drawing Sheets

ORAL AIRWAY DEVICES AND METHODS FOR MAKING AND USING THEM

This application claims benefit of U.S. provisional application Ser. No. 61/452,116, filed Mar. 13, 2011, and 61/559,244, filed Nov. 14, 2011, the entire disclosures of which are expressly incorporated by reference herein.

FIELD OF THE INVENTION

The present invention relates generally to oral airway devices, e.g., for introduction into a patient's oral cavity to facilitate performing a medical procedure, for example, for performing an endoscopic or other procedure where the patient's gastrointestinal system and/or other body regions are accessed through the oral cavity.

BACKGROUND

There are many medical procedures where a patient's body is accessed through their oral cavity, e.g., during procedures involving access into the gastrointestinal ("GI") system, airways, or other body cavities (e.g., a NOTES procedure) of the patient. For example, an endoscope or gastroscope may be introduced into a patient's oral cavity, and through the pharyngeal region, e.g., through the pharynx and into the esophagus, to observe and/or perform procedures involving organs within the GI system. One of the risks of such procedures is that the patient may accidentally bite down on the endoscope, which may risk damaging the endoscope and/or injuring the patient.

To reduce such risks, bite blocks may be provided, which are relatively short sleeves configured to be placed through the mouth into the oral cavity. The bite blocks may be sized to hold the mouth open and include a passage for introducing an endoscope therethrough into the oral cavity. The bite blocks may include a flange on one end that may be placed against or adjacent the patient's teeth to prevent the bite block from passing entirely into the oral cavity.

Thus, the bite block may protect the endoscope from damage, e.g., if the patient accidentally bites down during a procedure. Bite blocks, however, still require introducing an endoscope from the oral cavity into the patient's oropharynx, esophagus, and the like, which may require substantial manipulation by the physician or other user to navigate from the oral cavity to the desired location.

In addition or alternatively, a flexible or rigid airway tube may be introduced through a bite block and/or directly into the patient's oral cavity, e.g., into the pharynx or other desired location. An endoscope may then be introduced through the airway tube to access the patient's GI system. Such airway tubes, however, may present substantial frictional resistance to advancement of an endoscope, particularly if the airway tube includes sharp bends or buckles at natural bends in the patient's anatomy.

In addition, bite blocks do not provide a convenient way to monitor the patient's breathing and/or introducing fluids into the oral cavity. For example, generally, a nasal cannula may be used in combination with a bite block or otherwise to deliver oxygen to the patient, as needed during an endoscopic procedure. Such a cannula, however, may not deliver oxygen easily through restrictive tissues, such as the nasal sinuses or the oropharynx, e.g., if soft tissues, such as the tongue, soft palate, and the like, collapse due to sedation. Thus, oxygen delivered via a nasal cannula may not adequately reach the patient's lungs.

Accordingly, devices that facilitate access into the oral cavity, e.g., to introduce endoscopes, and/or otherwise perform medical procedures via the oral cavity, would be useful.

SUMMARY

The present invention is directed generally to oral airway devices, e.g., for introduction into a patient's oral cavity to perform a medical procedure, for example, to facilitate an endoscopic or other procedure where the patient's gastrointestinal system or other body regions are accessed via the oral cavity.

In accordance with one embodiment, an airway device is provided for introducing an endoscope, gastroscope, bronchoscope, trans-esophageal echocardiography instrument, or other device into a patient's gastrointestinal system or other body region, e.g., into the pharynx, esophagus, stomach, lungs, and the like. Generally, the airway device includes a proximal portion sized for placement in an oral cavity, a curved distal portion sized to be received within the oropharynx, and an instrument passage therebetween for receiving an endoscope or other device therethrough. For example, the proximal portion may be a tubular body defining an enclosed passage, and the distal portion may have a "C" shaped wall defining a channel extending from the enclosed passage to a distal tip of the distal portion.

Optionally, the proximal portion may include a flange for placement adjacent the patient's teeth when the airway device is inserted into the oral cavity. In addition or alternatively, the airway device may include one or more additional lumens, e.g., sampling, aspiration, and/or fluid delivery lumens, e.g., including ports on the face of the flange. For example, a sampling lumen may be provided that includes a connector port in the flange, and an inlet port located at a desired location along the instrument passage, e.g., within the enclosed passage of the proximal portion. In addition or alternatively, a fluid delivery lumen may be provided that includes a connector port on the flange and an outlet port communicating with the channel such that the outlet port is offset distally relative to the inlet port.

In an exemplary embodiment, the sampling lumen may be used to monitor carbon dioxide levels, e.g., from exhalation by the patient, and the fluid delivery lumen may be used to deliver oxygen into the patient's oropharynx. Optionally, the fluid delivery lumen may also be used to aspirate material, e.g., from the patient's oropharynx, or, alternatively, the airway device may include a separate aspiration lumen. By separating the inlet port of the sampling lumen from the outlet port of the fluid delivery lumen, more accurate variations in carbon dioxide levels may be monitored. Further, placing the outlet port adjacent the distal tip of the airway device may deliver oxygen more closely to the pharynx, which may enhance delivery of oxygen into the lungs, e.g., as compared with conventional nasal cannula devices.

In accordance with another embodiment, an airway device is provided for introducing an instrument into a patient's body via the patient's oral cavity that includes a tubular proximal portion sized for placement in an oral cavity and including an enclosed passage extending from a proximal end thereof for receiving an instrument therethrough and defining a central longitudinal axis. A "U" shaped transition portion may extend from the proximal portion that includes a partially enclosed passage communicating with the enclosed passage, and a curved distal portion may extend distally from the transition portion to a distal end.

The distal portion may include a "C" shaped wall defining a channel communicating with the partially enclosed passage and extending to the distal end, the wall of the distal portion defining an arc that is smaller than a periphery of the transition portion. For example, the transition portion may include lower edges that extend substantially parallel to the longitudinal axis, e.g., below the lower edges of the wall of the distal portion. In addition, the lower edges of the transition portion may extend generally parallel to a lower wall of the proximal portion or may be located further from the longitudinal axis than a lower wall of the proximal portion. For example, the lower edges of the transition portion may be spaced apart from one another by a predetermined distance and/or may have sufficient length to suppress or otherwise substantially stabilize a tongue of a patient when the airway device is introduced into the patient's oral cavity.

In accordance with still another embodiment, a system is provided for facilitating access into a patient's body via the patient's oral cavity that includes an airway device, a source of fluid, and a respiratory monitoring device. The airway device may include a tubular proximal portion sized for placement in an oral cavity and a curved distal portion extending distally from the proximal portion. The proximal and distal portions may together define an instrument passage for receiving an instrument therethrough extending from a proximal end of the proximal portion to a distal end of the distal portion.

A sampling lumen may extend from a sampling port on the proximal end to an inlet port communicating with the passage, and a fluid delivery lumen may extend from a fluid delivery port on the proximal end to an outlet port communicating with the passage such that the inlet port is located closer to the proximal end than the outlet port. The source of fluid may be coupled to the fluid delivery port for delivering fluid through the fluid delivery lumen and out the outlet port, and the respiratory monitoring device may be coupled to the sampling port for sampling respiratory gases via the inlet port. In an exemplary embodiment, the outlet port may be located in the distal portion and the outlet port may be located in the proximal portion.

In accordance with yet another embodiment, a method is provide for accessing a patient's body via the patient's oral cavity using an airway device that includes a tubular proximal portion and a curved "C" shaped distal portion extending distally from the proximal portion. The distal portion of the airway device may be introduced into the patient's oral cavity towards the pharyngeal region until a proximal end of the proximal portion is located adjacent the patient's mouth, e.g., until a proximal portion enters the oral cavity and/or flange on the proximal end is disposed adjacent the patient's teeth. A distal end of an instrument may be introduced through an enclosed passage in the proximal portion and into a "C" shaped channel of the distal portion to introduce the instrument distal end into the pharyngeal region.

In one embodiment, a distal tip of the airway device may include a recess therein, and when the instrument distal end is introduced into the channel, the instrument distal end may be directed along the channel and through the recess such that the instrument distal end has a greater radius of curvature than the distal portion of the airway device.

Optionally, the airway device may include a transition portion between the proximal and distal portions having a "U" shaped cross-section including lower edges adjacent the inside of the curve of the distal portion. Consequently, when the distal portion of the airway device is introduced into the oral cavity, the lower edges may be positioned adjacent the patient's tongue to substantially stabilize the tongue.

In addition or alternatively, the method may include delivering one or more fluids into the oral cavity and/or pharyngeal region, aspirating fluids therefrom, and/or monitoring one or more physiological parameters of the patient using the airway device. For example, in one embodiment, oxygen or other fluid may be delivered via a fluid delivery lumen on the airway device, e.g., such that the oxygen or other fluid exits an outlet port in the distal portion into the channel. In addition or alternatively, one or more gas concentrations of respiratory air of the patient may be monitored from an inlet port in the airway device. In an exemplary embodiment, the inlet port may be located closer to the proximal end of the airway device than the outlet port of the fluid delivery lumen, e.g., to reduce false concentration readings from the inlet port due to exposure to the fluid delivered via the outlet port.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1A:
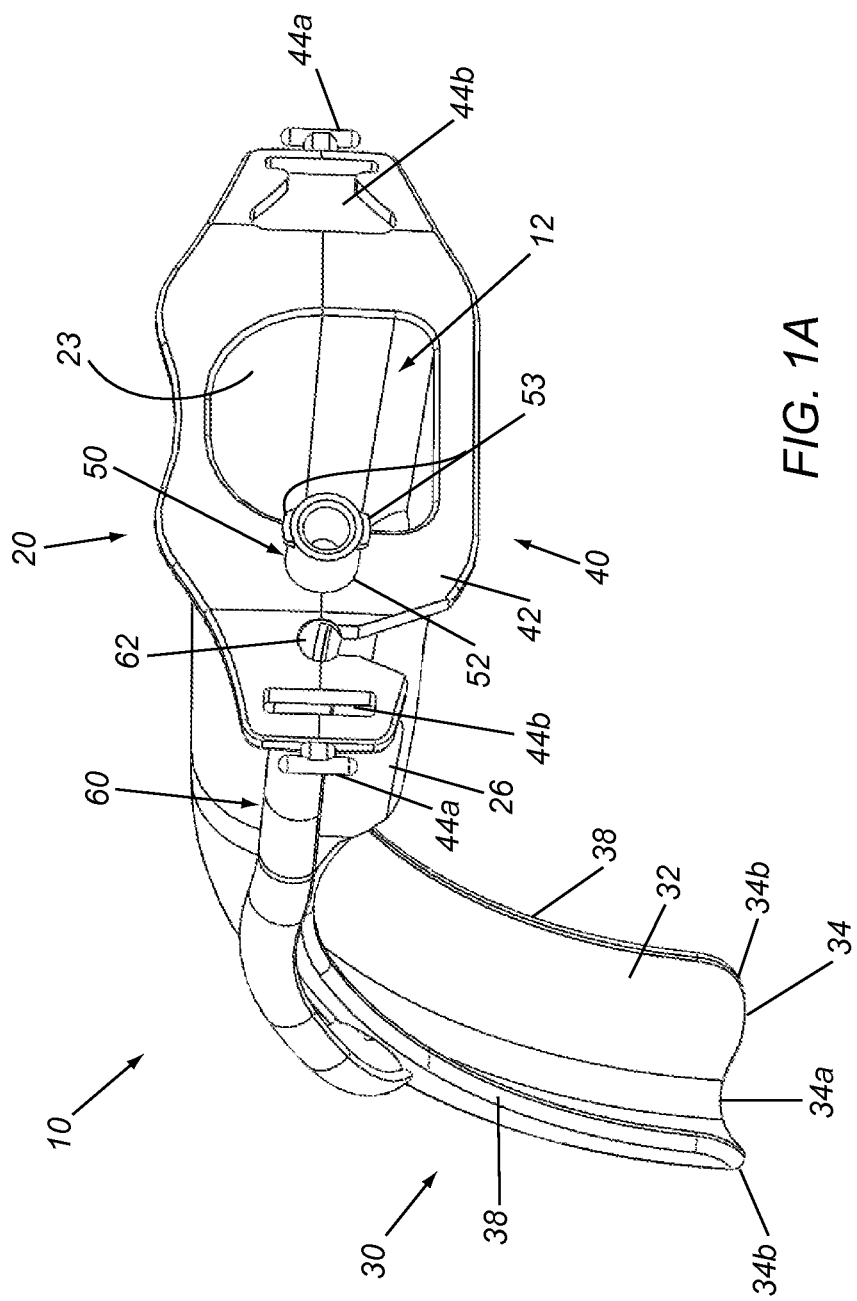
FIGS. 1A and 1B are perspective views of an exemplary embodiment of an airway device that may be positioned within an oral cavity of a patient.
Figure 1B:
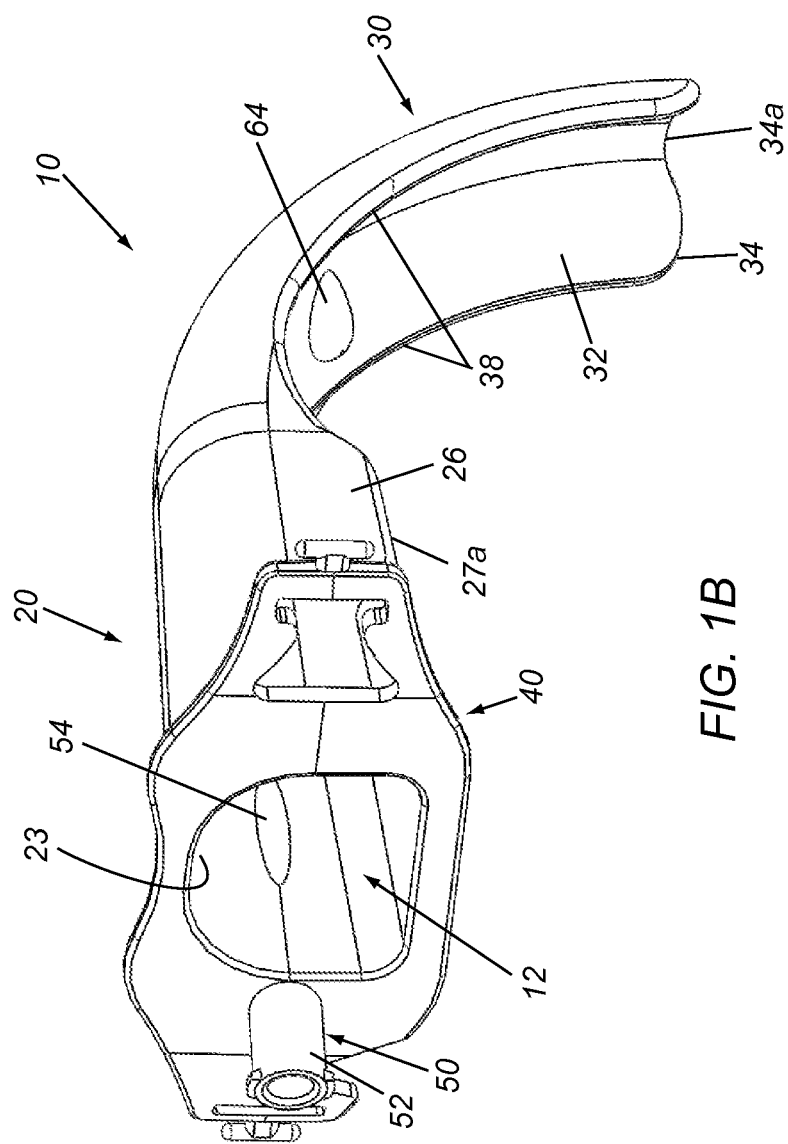
Figure 1C:
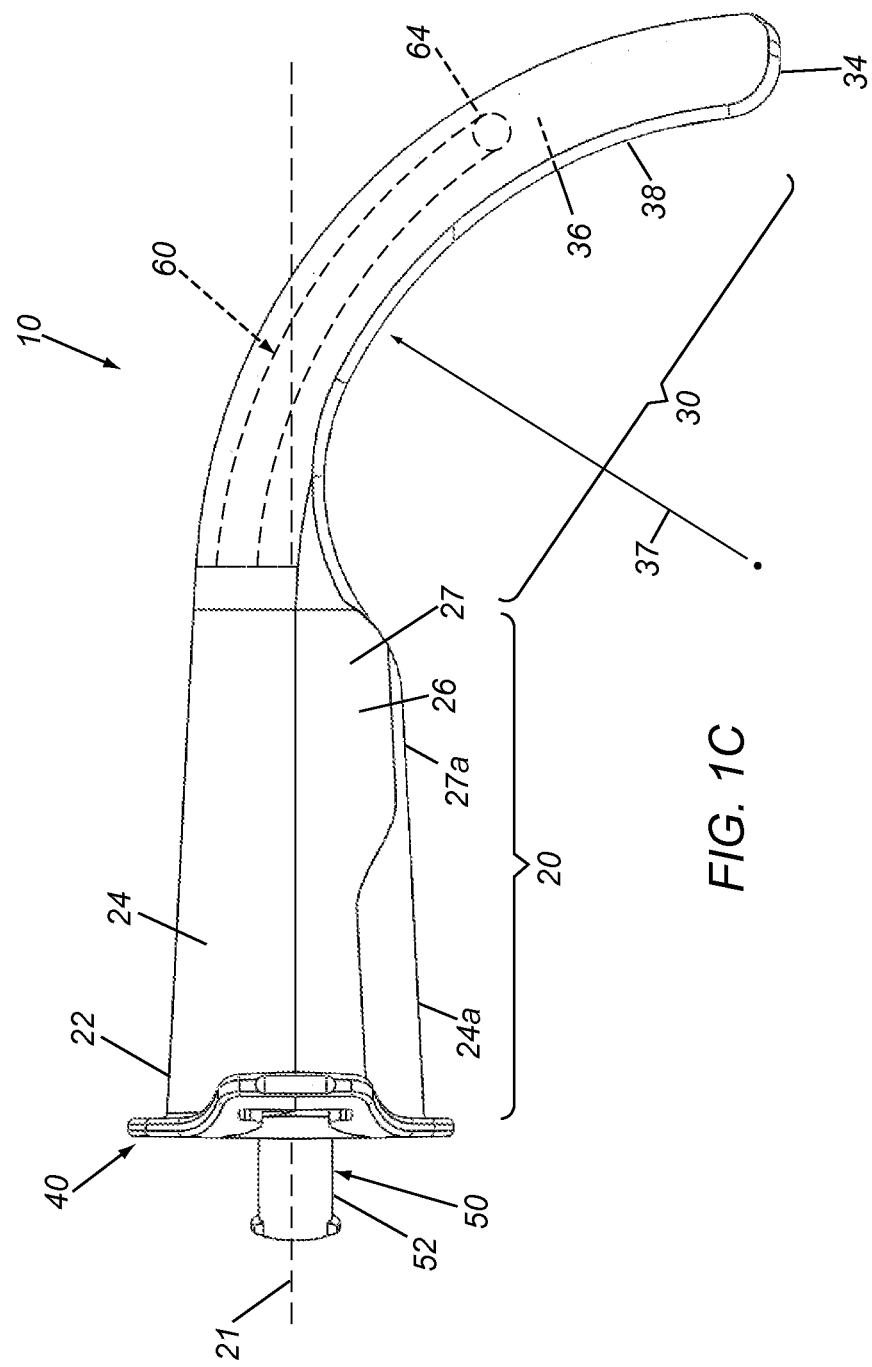
FIGS. 1C and 1D are side views.
Figure 1D:
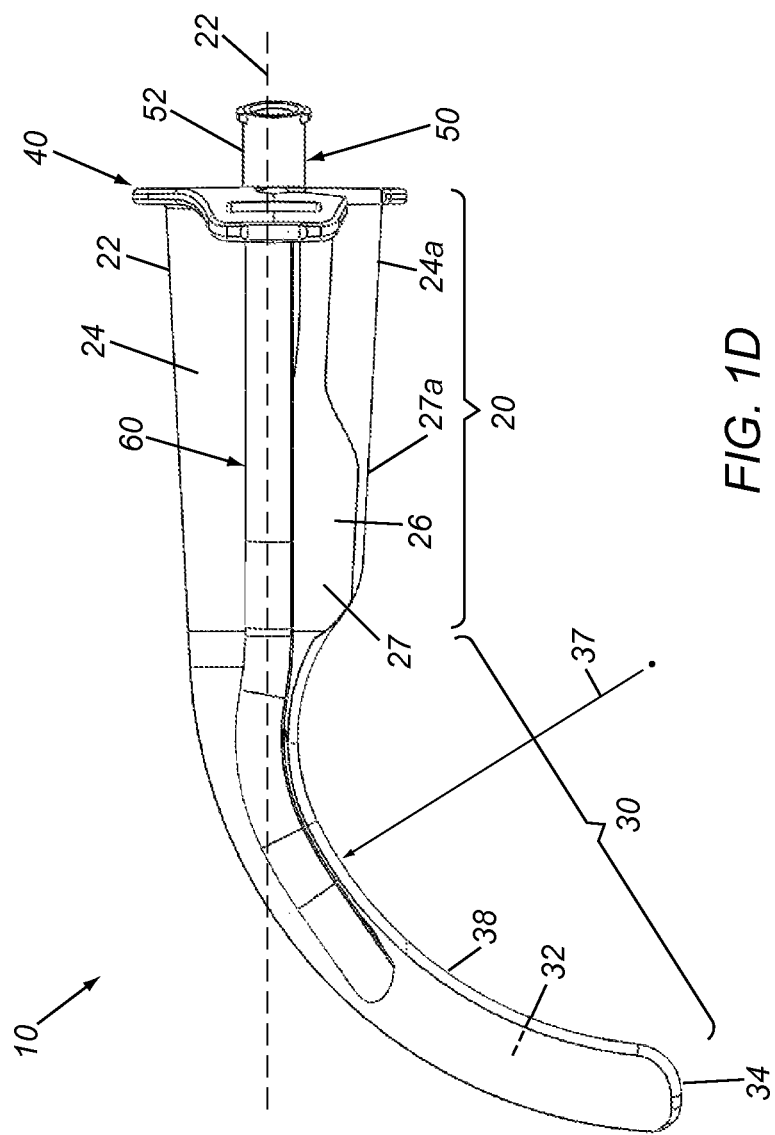
Figure 1E:
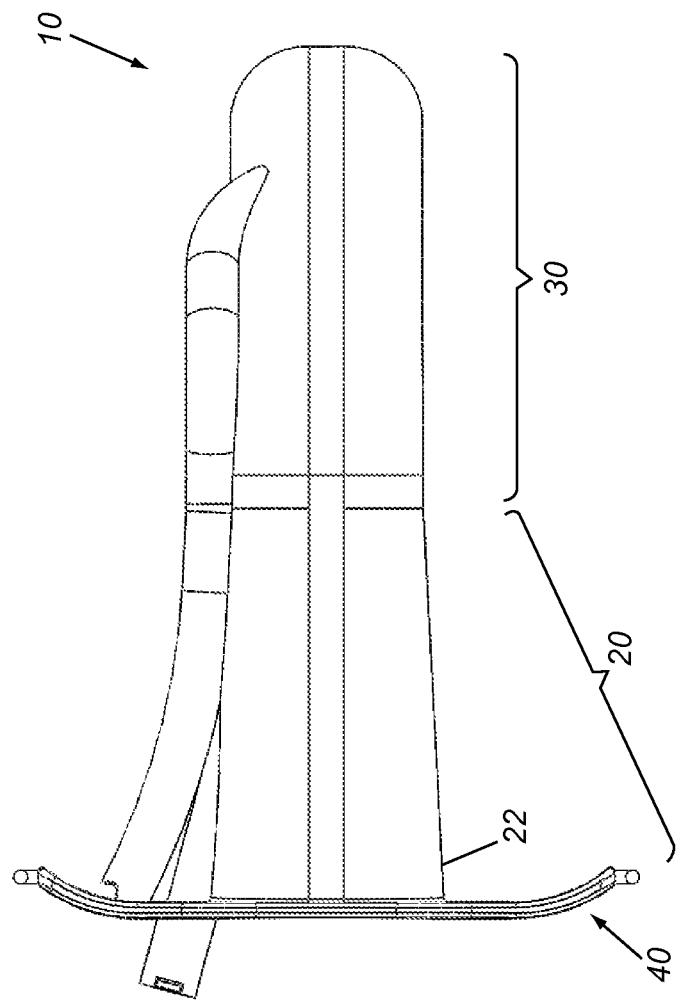
FIGS. 1E-1G are top, bottom, and front views, respectively, of the airway device of FIGS. 1A and 1B.

Turning to the drawings, FIGS. 1A-1G show an exemplary embodiment of an airway device 10 for introducing an endoscope, gastroscope, bronchoscope, ultrasound probe, transesophageal echocardiography instrument, or other device (not shown) into a patient's gastrointestinal, respiratory system, or other body cavity, e.g., into the pharynx, esophagus, stomach, lungs, and/or other organs or regions accessible via the GI or respiratory systems and/or otherwise via the patient's oral cavity. As shown, the airway device 10 includes a generally straight proximal portion 20 and a curved distal portion 30 extending from the proximal portion 20, e.g., as best seen in FIGS. 1C and 1D, thereby defining an instrument passage 12 for receiving an endoscope or other device therethrough. In addition, the airway device 10 may include one or more additional tubes or lumens, e.g., lumens 50, 60, that are at least partially isolated from the instrument passage 12 and/or extend at least partially along the proximal portion 20 and/or the distal portion 30, as described further below. Alternatively, the airway device may include separate airway and instrument passages (not shown), such that an endoscope or other device may be introduced into the instrument passage, while the patient continues to breathe freely through the airway passage, as described further elsewhere herein.

Generally, the proximal portion 20 includes a flange 40, e.g., extending radially outwardly from a proximal end 22 of the proximal portion 20. The flange 40 may include one or more ports, e.g., communicating with respective lumens extending from the proximal end 22. For example, as best seen in FIGS. 1A and 1B, the airway device 10 may include a sampling lumen 50, e.g., extending from a connector port 52 on the face 42 of the flange 40, and an oxygen, gas, or other fluid delivery lumen 60, e.g., extending from a port 62 adjacent the face 42 of the flange 40. One or both of the ports 52, 62 may extend outwardly from the face 42 of the flange 40, may be flush with the flange 40, and/or may be recessed within or behind the flange 40, as desired.

The proximal portion 20 may be sized for placement in an oral cavity, e.g., having a predetermined cross-section sized to be placed into the patient's mouth and maintaining the mouth open, and a predetermined length to extend into the oral cavity, e.g., over or along the tongue and/or towards the back of the throat (not shown). Optionally, as shown, the proximal portion may taper from its proximal end 22 towards the distal portion 30, e.g., to provide a more comfortable or anatomical transition from the proximal end 22 towards the distal portion 30.

The flange 40 may be substantially planar and/or larger than the proximal end 22, e.g., such that the flange 40 may be positioned adjacent or against the patient's teeth when the airway device 10 is introduced into the oral cavity, e.g., to prevent the entire airway device 10 from passing into the oral cavity. Optionally, the flange 40 may include one or more features for securing the airway device 10 relative to a patient, e.g., one or more tabs 44a or pockets 44b for receiving ends of straps (not shown) that may be placed around the patient's head to secure the airway device 10. Alternatively, the flange 40 may be omitted, if desired, e.g., which may allow the proximal portion 20 to be placed entirely within the oral cavity.

Figure 1F:
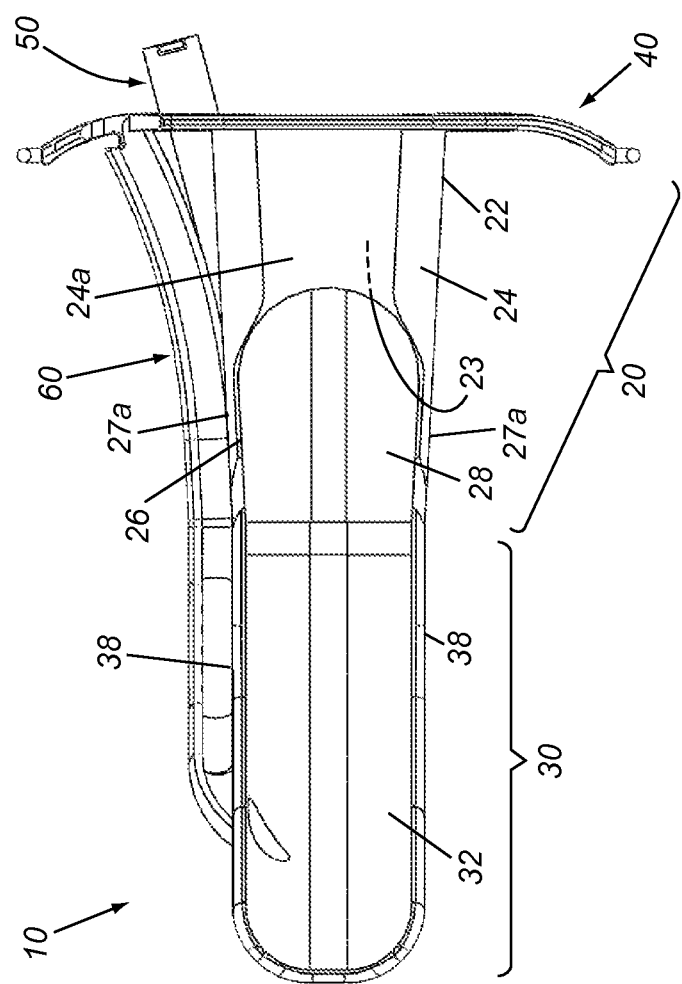
Figure 2A:
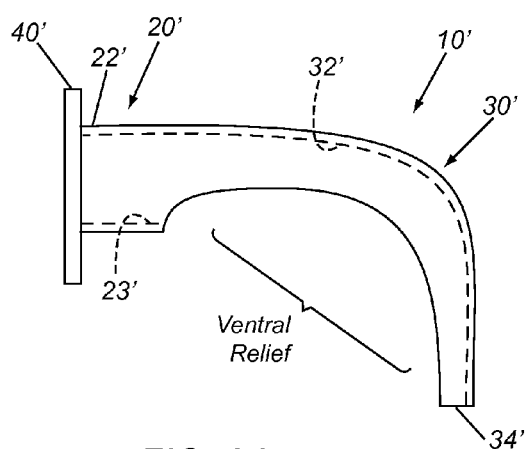
FIGS. 2A and 2B are side and back views of an alternate embodiment of an airway device, similar to that shown in FIGS. 1A-1G.
Figure 2B:
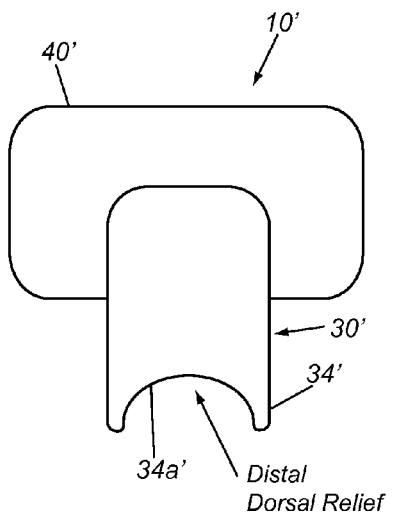
Figure 2C:
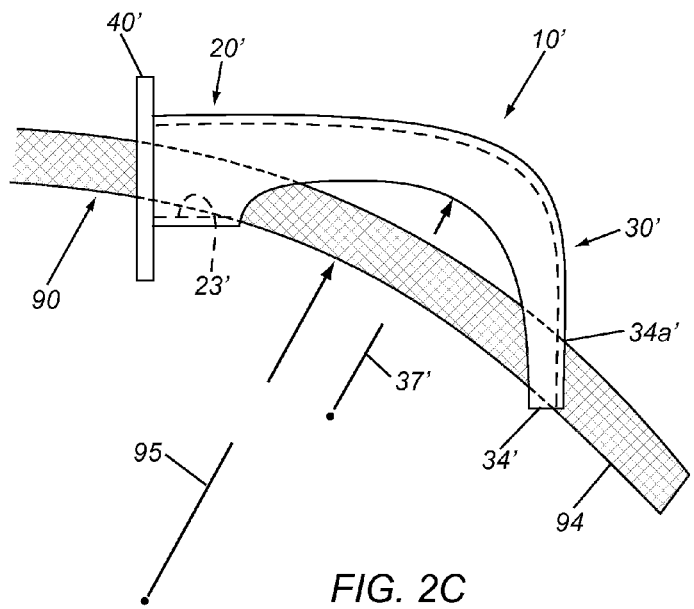
FIG. 2C is a side view of the airway device of FIGS. 2A and 2B, with an endoscope inserted through an instrument passage of the airway device.

As best seen in FIG. 1F, the proximal portion 20 may include an enclosed region 24 extending distally from the proximal end 22 towards the distal portion 30, thereby defining an enclosed passage 23, and an inverted "U" shaped or other arcuate transition region 26 between the enclosed region 24 and the distal portion 30, e.g., defining a partially enclosed passage 28. The transition region 26 may include side walls 27 that extend downwardly to define lower edges 27a, as best seen in FIGS. 1C and 1D. The side walls 27 may be substantially flat, may curve greater than one hundred eighty degrees (180°), or may be otherwise shaped to partially enclose the passage 28 and provide the lower edges 27a. Alternatively, as shown in FIGS. 2A-2C, an airway device 10' may be provided that does not include the transition region 26 (but may otherwise be similar to the airway device 10 or any of the other embodiments herein).

Returning to FIGS. 1C and 1D, the lower edges 27a may extend generally parallel to a central longitudinal axis 21 of the proximal portion 20. As shown in FIG. 1C, the lower edges 27a may be substantially coextensive with a lower surface 24a of the enclosed region 24 and/or may be spaced apart from one another by a predetermined distance, such that the lower edges 27a may facilitate suppressing or otherwise substantially stabilizing a tongue and/or other anatomy of a patient within whose oral cavity the airway device 10 is introduced, e.g., to facilitate keeping the passage 28 open, as described further elsewhere herein. Alternatively, as shown in FIG. 1D, the side walls 27 of the transition region 26 may have a greater height than side walls of the enclosed region 24 (not shown), e.g., such that the lower edges 27a extend below the lower surface 24a, which may enhance stabilization of the tongue or other tissue within the oral cavity (also not shown).

The length of the enclosed region 24 may be relatively short compared to the overall length of the airway device 10, e.g., between about one and six centimeters (1-6 cm). For example, the enclosed region 24 may simply be sufficiently long to pass between the patient's teeth into the oral cavity such that, if the patient bites down on the airway device 10, only the enclosed region 24 is contacted, e.g., to provide a substantially smooth contact surface without abrupt edges (unlike the transition region 26 and the distal portion 30). The enclosed passage 23 of the enclosed region 24 may have a diameter or other cross-section large enough to receive an endoscope or other device therethrough, e.g., between about one and four centimeters (1-4 cm). The enclosed region 24 may have a generally elliptical, oblong, or other asymmetrical shape, e.g., having a width greater than its height, e.g., such that the size of the enclosed passage 23 is maximized while minimizing discomfort for the patient. Alternatively, the enclosed passage 23 may have a substantially circular or other cross-section to facilitate introduction of an endoscope or other instrument therethrough, as described elsewhere herein.

The length of the transition region 26 may be sufficient to extend towards the back of the patient's throat and/or over the patient's tongue, e.g., between about one and six centimeters (1-6 cm). For example, the lower edges 27a may be sufficiently long and spaced apart from one another to restrain the patient's tongue, e.g., to prevent the tongue from entering the passage 28 and/or rolling back into the patient's throat. Alternatively, the transition region 26 may be omitted, e.g., by extending the enclosed region 24 or shortening the entire proximal portion 20, e.g., as shown in FIGS. 2A-2C.

With continued reference to FIGS. 1A-1D, the curved distal portion 30 extends distally from the proximal portion 20, e.g., from the transition region 26, and may have a generally "C" shaped or other arcuate wall defining a channel 32 extending from the passage 28 to a distal tip 34 of the distal portion 30. As shown, the open side of the channel 32 may be oriented inwardly towards the center of the radius of curvature 37 of the distal portion 30 and the wall may be oriented along the outside of the curvature, e.g., to protect tissues adjacent the wall during introduction of an endoscope or other device, as described further elsewhere herein. Thus, together, the channel 32, the partially enclosed passage 28, and the fully enclosed passage 23 may define the instrument passage 12 of the airway device 10 extending from the proximal end 22 to the distal tip 34.

Alternatively, the distal portion 30 (e.g., with the transition region 26 omitted) may also be a tubular body (not shown), similar to the enclosed region 24 of the proximal portion 20. Thus, the channel 32 may be fully enclosed and may communicate directly with and/or may be coextensive with the enclosed passage 23. In this alternative, the instrument passage 12 may have a substantially uniform diameter or other cross-section and/or may be tapered, e.g., such that the instrument passage 12 is smaller within the distal portion 30 than within the proximal portion 20.

Returning to FIGS. 1A, 1B, 1F, and 1G, the cross-section of the wall of the distal portion 30 may have a uniform or variable radius of curvature 36 across its width as best seen in FIG. 1F, e.g., defining an arc or curve defining an angle of less than ninety degrees (90°), e.g., between about forty five and ninety degrees (45-90°). For example, as best seen in FIGS. 1C and 1D, the wall of the distal portion 30 may define a smaller arc or curve than the transition region 26, e.g., such that lower edges 38 of the distal portion 30 may be offset upwardly from the lower edges 27a of the transition region 26 of the proximal portion 20. Thus, the distal portion 30 may have a smaller width or other profile, which may facilitate introduction of the distal portion 30 into the oropharynx or hypopharynx region of a patient.

In addition, the distal portion 30 may define a substantially uniform or variable radius of curvature 37 between the transition region 26 and the distal tip 34, e.g., as shown in FIGS. 1C and 1D. The curvature and length of the distal portion 30 may correspond generally to the anatomy of the pharyngeal region of patients, e.g., such that the distal tip 34 may be located adjacent the pharynx (not shown) when the airway device 10 is properly introduced into the oral cavity of a patient.

Figure 1G:
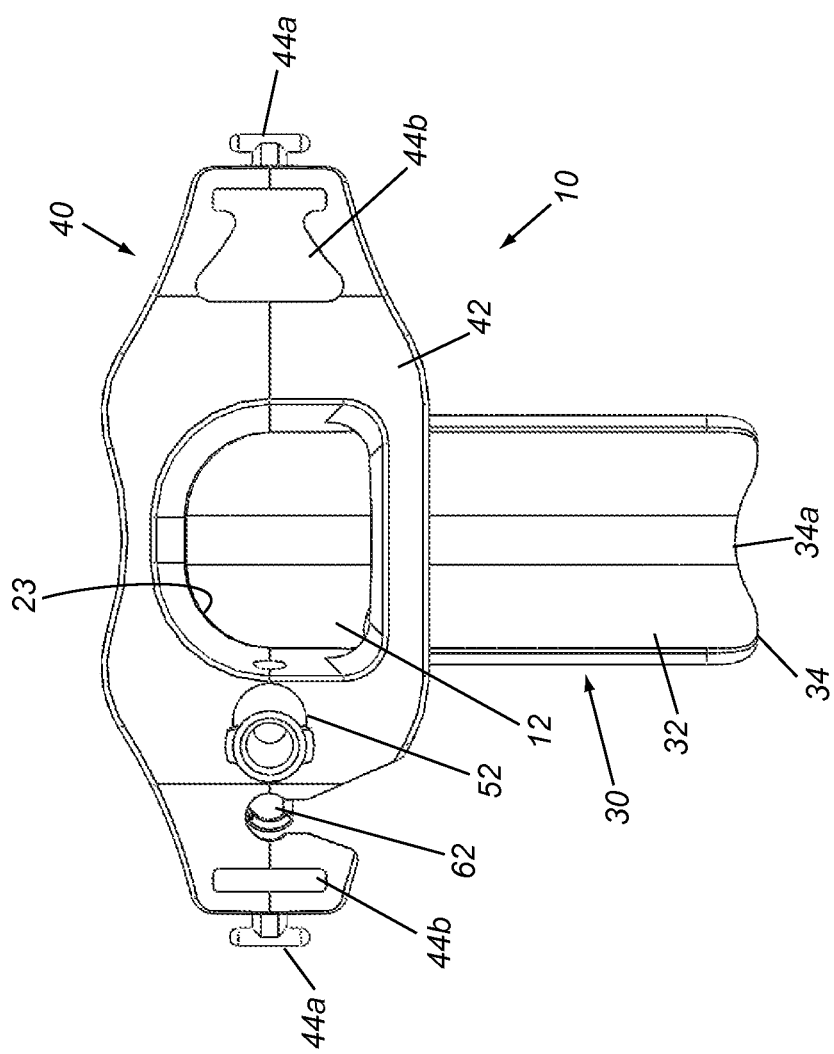

The distal tip 34 may be rounded or otherwise substantially atraumatic, e.g., to facilitate introduction of the distal portion 30 through the oral cavity and into the pharyngeal region without substantial risk of damaging surrounding tissue. Optionally, as best seen in FIGS. 1A, 1B, and 1G, the distal tip 34 may include a recess 34a extending proximally therefrom, e.g., a curved, atraumatic recess between rounded distal tabs 34b. For example, as shown in FIGS. 2A-2C and described further below, the recess 34a' may facilitate introduction of an endoscope or other device 90 through the airway device 10,' e.g., at a larger radius of curvature 95 than the radius of curvature 37' of the distal portion 30.'

The airway device 10 may include one or more additional lumens or passages in addition to or instead of the instrument passage 12, e.g., a sampling lumen 50 and a fluid delivery lumen 60, as shown. In addition or alternatively, the airway device 10 may also include an aspiration lumen extending from the proximal end 22 to the distal tip 34, for example, to facilitate aspiration of secretions from the oral cavity or pharynx.

In an exemplary embodiment best seen in FIGS. 1A and 1B, the sampling lumen 50 may extend between the connector port 52 on the flange 40 and an inlet 54 communicating with the passage 12, e.g., within the enclosed passage 23 of the proximal portion 20 immediately adjacent the proximal end 22. Alternatively, the sampling inlet 54 may be provided at other locations (entering inside and/or outside) along the instrument passage 12, e.g., within the partially enclosed passage 28 or within the channel 32. In a further alternative, if the airway device includes separate instrument and airway passages (not shown), the sampling inlet 54 may communicate with the airway passage, rather than the instrument passage.

For example, a section of tubing or other sampling line (not shown) may be coupled to the connector port 52 on the flange 40, which may communicate with a monitoring device (also not shown) for monitoring levels of carbon dioxide and/or other parameters of air exhaled by the patient. Optionally, the connector port 52 may include one or more connectors 53, e.g., beveled tabs, rings, barbs, a Luer fitting, and the like, which may enhance securing, sealing, or otherwise coupling tubing to the sampling lumen 50.

Exhalation air may be periodically or substantially continuously monitored, for example, drawing air into the sampling inlet 54, through the sampling lumen 50 and into the sampling line to the monitoring device, e.g., to approximate carbon dioxide levels when the patient exhales and/or simply to measure pressure changes within the enclosed passage 23. It may not be necessary to monitor carbon dioxide levels (or pressure) accurately, and instead, the monitoring device may simply monitor changes in the carbon dioxide levels (or pressure), e.g., over time and/or during individual breathing cycles, to confirm that the patient is breathing normally.

The sampling inlet 54 may be oriented substantially perpendicular to a side wall of the proximal portion 20, or may be angled, e.g., towards the proximal end 22 or towards the distal portion 30, if desired to facilitate drawing exhalation gas into the sampling lumen 50. In addition or alternatively, the sampling inlet 54 may have a widened mouth and/or tapered shape compared to the inner diameter of the sampling lumen 50, e.g., to reduce the risk of the inlet 54 being obstructed by fluids, secretions, lubricants, or other materials that may enter the passage 23, and/or to provide a low pressure loss of sample gases being drawn into the sampling lumen 50. For example, if the sampling inlet 54 communicates with the enclosed passage at an angle, e.g., less than ninety degrees (90°) or even less than forty five degrees (45°), the inlet 54 may have a longer width than height, as best seen in FIG. 1B, thereby providing a relatively large inlet 54 compared to the sampling lumen 50.

In addition or alternatively, the airway device 10 may include one or more other sensors (not shown) for measuring physiological parameters of the patient. For example, a pulse oximeter sensor (not shown) may be included in a region of the airway device 10 that may contact mucous membranes or other tissues adjacent the oral cavity, e.g., to measure oxygen saturation levels via the contacted tissues. Optionally, a thermocouple or other temperature sensor (also not shown) may be provided on the airway device 10 for measuring temperature within the oral cavity. Such a temperature sensor may be provided on an exterior surface of the airway device 10 or otherwise away from any passage through which fluid may flow, e.g., to reduce the risk of false temperatures being detected based on the fluids rather than the patient's body. Alternatively, the temperature sensor may be provided within the instrument passage 12, e.g., to monitor variations in temperature of respiratory gases.

With particular reference to FIGS. 1A, 1B, and 1G, the fluid delivery lumen 60 may extend between the connector port 62 on the flange 40 and an outlet port 64, e.g., in the distal portion 30. As shown, the connector port 62 may be an aperture, e.g., in the flange 40, which may slidably or otherwise receive tubing or other sources of oxygen or other gas or fluid (not shown). Optionally, the connector port 62 may include one or more features for securing tubing inserted into the connector port 62, similar to the connector port 52. Alternatively, the connector port 62 may include a nipple, barbed fitting, or other connector, e.g., a Luer fitting (not shown), extending from the face 42 of the flange 40, similar to the connector port 52 of the sampling lumen 50. Alternatively, a length of extension tubing (not shown) may be provided instead of the connector port 62 (and/or to the connector 52), which may include a connector on its free end, e.g., to facilitate connecting the tubing to a source of fluid (not shown).

As best seen in FIGS. 1A, 1B, and 1G, the connector ports 52, 62 of the sampling and fluid delivery lumens 50, 60 may be located on the same side of the flange 40. Such a configuration may facilitate accessing both connector ports 52, 62 from one side of the patient. In particular, positioning the lumens 50, 60 on the left side of the airway device 10, as shown, may facilitate positioning the patient in a left lateral decubitus position, while allowing tubes extending from the connector ports 52, 62 to conveniently pass over the patient's ear and out of the way of the patient's face. Alternatively, the connector ports 52, 62 may be provided on opposite sides of the flange 40 (not shown), e.g., on left and right sides of the flange 40, which may facilitate distinguishing the connector ports 52, 62 from one another. Similarly, the inlet and outlet ports 54, 64 communicating with the passage 12 may be located on the same side or different sides of the proximal and distal portions 20, 30 of the airway device 10.

As best seen in FIGS. 1A and 1D-1F, the fluid delivery lumen 60 may extend along the proximal and distal portions 20, 30 adjacent to and substantially isolated from the passage 12 other than at the outlet port 64. The fluid delivery lumen 60 may be formed directly in the wall of the proximal and distal portions 20, 30, or may be a separate tube or other structure secured to outer or inner surfaces of the proximal and distal portions 20, 30, as described further elsewhere herein. As shown, the outlet port 64 may be located adjacent the distal tip 34 of the airway device 10, which may enhance delivery of oxygen (and/or other fluids) into the pharynx. For example, delivering oxygen adjacent the distal tip 34 may enhance delivery into the trachea and lungs, while reducing dryness and/or other problems that may arise when oxygen is delivered into the nasal sinuses or blown directly into tissue regions. Alternatively, if desired, the outlet port 64 may be located at other locations within the instrument passage 12, e.g., within the enclosed passage 23 or partially enclosed passage 26 (not shown).

Similar to the sampling inlet 54, the fluid delivery outlet 64 may have a widened mouth and/or tapered shape compared to the inner diameter of the fluid delivery lumen 60, e.g., to reduce the risk of the outlet 64 being obstructed materials that may enter the passage 23 and/or to diffuse delivered fluid. For example, the outlet 64 may communicate with the channel 32 at an angle less than ninety degrees (90°) or less than forty five degrees (45°), e.g., oriented towards the distal tip 34 or otherwise, for example, to direct oxygen or other fluid delivered through the outlet 64 towards the trachea or other desired anatomy of the patient.

In addition, in this configuration, the outlet port 64 of the fluid delivery lumen 60 may be spaced distally from the inlet port 54 of the sampling lumen 50. For example, by placing the inlet port 54 of the sampling lumen 50 adjacent the opposite end of the airway device 10 from the outlet port 64 of the fluid delivery lumen 60, more accurate carbon dioxide readings may be obtained. In contrast, if the inlet and outlet ports were located close to one another, the sampling lumen may simply draw in oxygen or other gas from the fluid delivery lumen, which may cause inaccurate readings of the carbon dioxide levels.

Alternatively, the sampling lumen 50 may extend to the distal portion 30, e.g., such that the sampling inlet 54 is disposed adjacent the outlet port 64, for example, directly opposite the outlet port 64 (not shown). In this alternative, if pure oxygen (or other gas without carbon dioxide) is delivered into the outlet port 64, the monitoring device may establish a baseline of little or no carbon dioxide, e.g., during inhalation, and may compare the baseline with carbon dioxide levels detected, e.g., during exhalation or even subsequent inhalation. The resulting trace may be used to confirm normal respiration of the patient, e.g., as a safety feature.

Figure 7A:
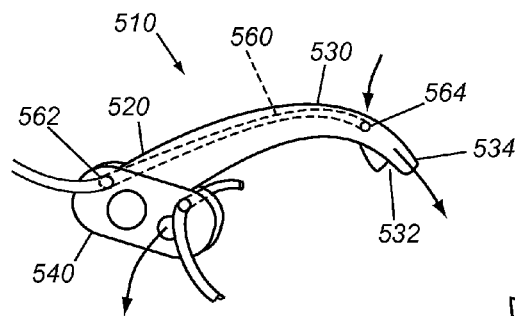
FIGS. 7A-7D are perspective, side, top, and front views, respectively, of another embodiment of an airway device.
Figure 7B:
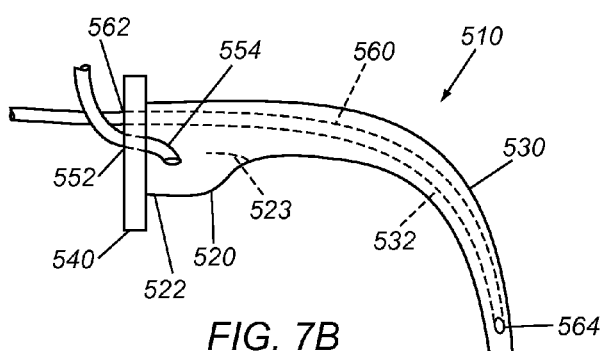

Optionally, to further facilitate carbon dioxide monitoring and/or oxygen delivery, a valve (not shown) may be provided within the airway device 10, e.g., within the proximal portion 20, similar to embodiments shown in FIGS. 7A-7B and described elsewhere herein.

Generally, the proximal and distal portions 20, 30 of the airway device 10 may be substantially rigid or semi-rigid. For example, the proximal portion 20 may be substantially rigid, e.g., to support the mouth of the patient substantially stationary in a desired open orientation and/or to prevent the proximal portion 20 from being compressed, e.g., if the patient bites down on the proximal portion 20, thereby protecting an endoscope and/or other devices are introduced into the passage. Alternatively, the material of the proximal portion 20 may be semi-rigid and/or compliant, e.g., to reduce risk of damage to the patient's teeth. In an exemplary embodiment, the enclosed region 24 of the proximal portion 20 may include a substantially rigid tubular base and a compliant ring or layer surrounding the tubular base (not shown), e.g., formed from urethane, silicone, or other elastomeric or compliant material, to provide comfort and/or protect the patient's teeth.

Similarly, the distal portion 30 may be substantially rigid such that the distal portion 30 maintains a predetermined curvature or other shape during introduction. Alternatively, the distal portion 30 may be semi-rigid to conform at least partially to the anatomy encountered with a particular patient, or the distal portion 30 may malleable such the physician may modify the radius of curvature, the arcuate shape of the side wall, or otherwise modify the configuration of the distal portion 30 as desired based upon the particular anatomy encountered.

Exemplary materials for the airway device 10 may include metals, such as stainless steel, plastics, such as polyethylene (e.g., HDPE or LDPE), nylon, thermoplastics (e.g., PVC), PEBAX, polypropylene, and the like, or composite materials. Optionally, inner surfaces of the airway device 10, e.g., defining one or more of the instrument passage 12, the sampling lumen 50, and/or the fluid delivery lumen 60, may include one or more coatings or other materials. For example, the inner surfaces of the instrument passage 12 may include a lubricious coating or material, which may reduce friction when an endoscope or other device is introduced through the instrument passage 12, such as a hydrophilic coating, a silicone lubricant, and/or a lubricious material, e.g., HDPE, FEP, PTFE, and the like.

In one embodiment, two or more components of the airway device 10 may be integrally formed as a single part. For example, the proximal and distal portions 20, 30, the flange 40, and the lumens 50, 60 may be molded, machined, cast, or otherwise formed as a single part.

Figure 3A:
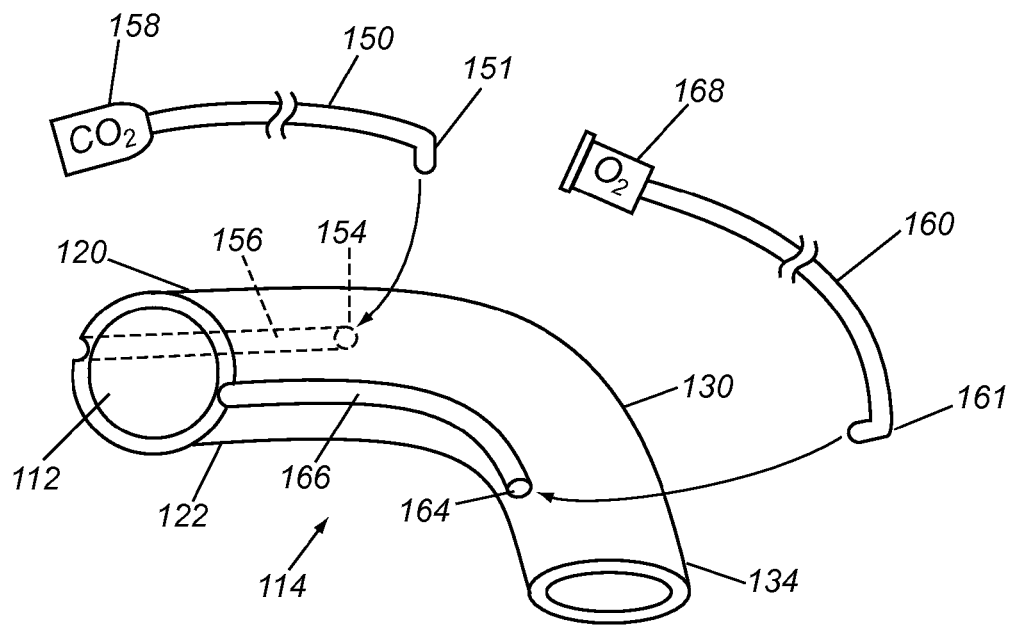
FIGS. 3A and 3B are perspective views of components of an airway device being assembled from a tubular body and separate lumens.
Figure 3B:
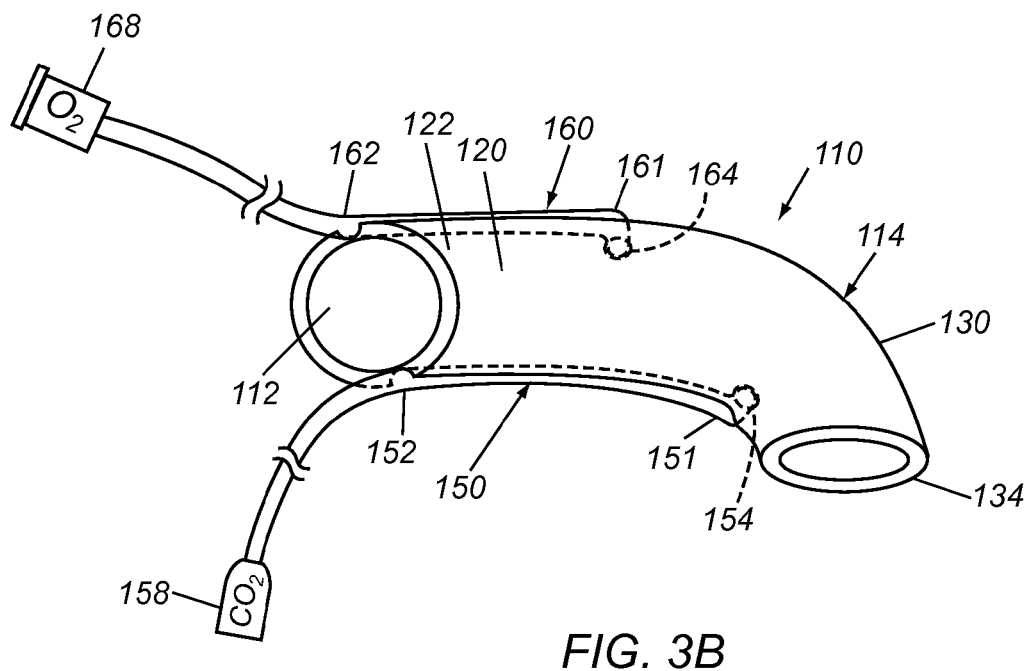

Alternatively, the airway device 10 may be formed from multiple components that are attached together or otherwise assembled into the final airway device 10. For example, as shown in FIGS. 3A and 3B, an airway device 110 is shown in which the proximal and distal portions 120, 130 are integrally formed as a single part, e.g., formed as a single tubular body 114 including an instrument passage 112. Sampling and fluid delivery lumens 150, 160 are provided as separate components, e.g., sections of flexible, semi-rigid, or rigid tubing, that may be attached to the tubular body 114.

For example, as shown in FIG. 3A, the outer surfaces of the tubular body 114 include grooves or recesses 156, 166 for receiving the lumens 150, 160. For example, the recesses 156, 166 and ports 154, 164 may be molded or cast along with the tubular body 114, or may be subsequently machined or otherwise formed in the wall of the tubular body 114 after it is formed. As shown in FIG. 3B, the lumens 150, 160 may be received within the recesses 156, 166, respectively, and attached to the tubular body 114, e.g., by one or more of a snap-fit or other interference fit, one or more connectors (not shown), bonding with adhesive, sonic or thermal welding or fusing, and the like.

As shown, the lumens 150, 160, may include first ends 151, 161 that may be attached to the ports 165, 164 in the tubular body 114, and second ends 152, 162 that may be attached to the proximal end 122 of the tubular body 114, e.g., to a flange (not shown), similar to other embodiments herein. In the embodiment shown in FIGS. 3A and 3B, the lumens 150,160 may include extensions of tubing that include connectors 158, 168, e.g., Luer fittings and the like, for coupling the lumens 150, 160 to other devices (not shown), similar to other embodiments herein.

Figure 4A:
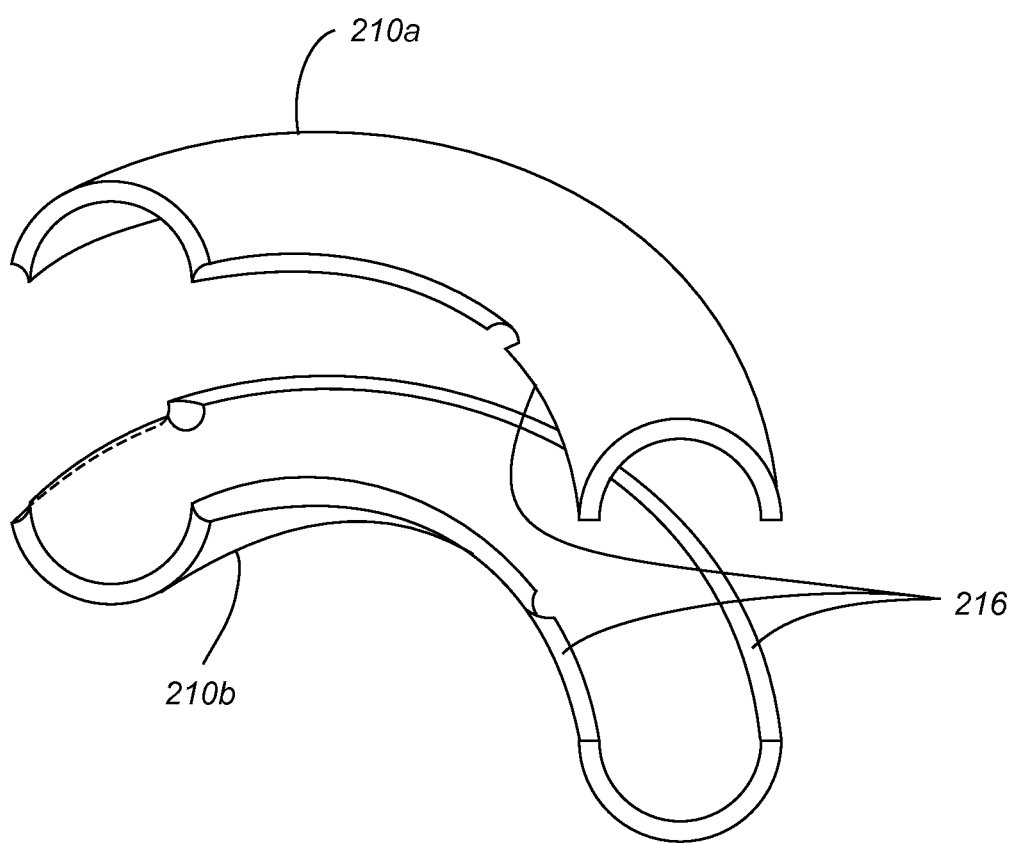
FIG. 4A is a perspective view of clam-shell components that may be assembled together to provide an airway device.
Figure 4B:
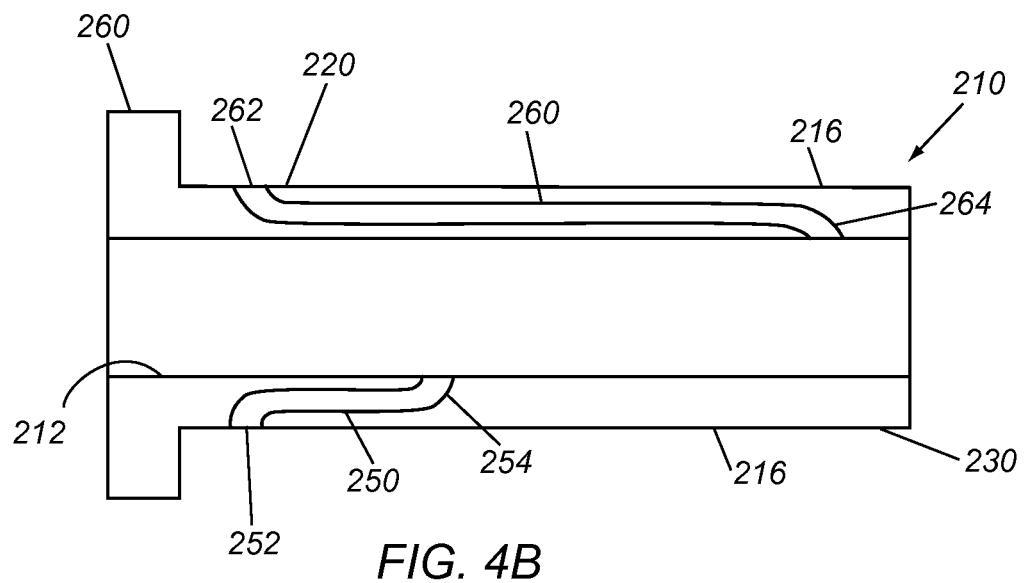
FIGS. 4B and 4C are cross-sectional and side views, respectively, of the airway device after assembly of the clam-shell components of FIG. 4A.
Figure 4C:
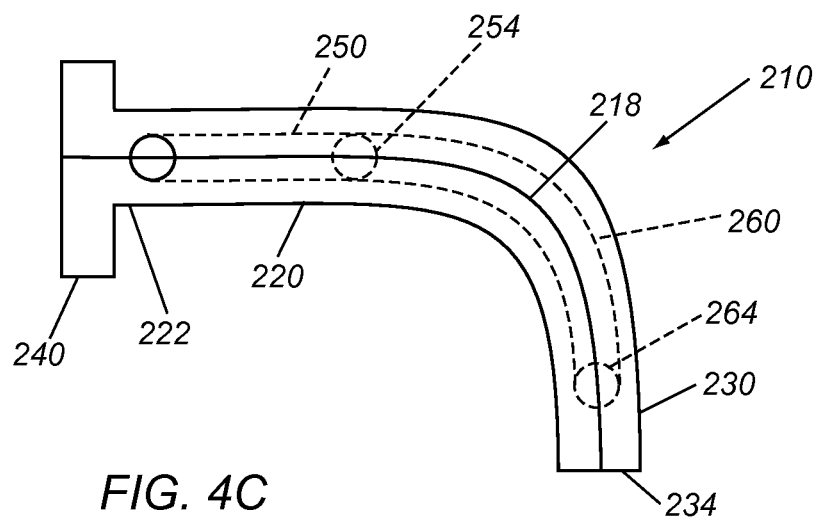

Alternatively, as shown in FIGS. 4A-4C, an airway device 210 may be formed as a pair of clam-shell components 210a, 210b, e.g., as shown in FIG. 4A, that may be attached together along opposing edges 216, e.g., to provide a pair of seams, e.g., as shown in FIG. 4C, extending along the length of the finished airway device 210, e.g., between the proximal end 22 and the distal tip 34. The clam-shell components may be attached together by one or more of cooperating connectors (not shown) along the opposing edges 216, bonding with adhesive, sonic or thermal welding or fusing, and the like.

In this alternative, the sampling lumen 250 and fluid delivery lumen 260 may be formed as recesses or grooves within the walls of the clam-shell components 210a, 210b, e.g., along the edges 216, which may be substantially enclosed when the clam-shell components 210a, 210b are attached together. Alternatively, the clam-shell components 210a, 210b may simply define recesses (not shown) into which separate lumens, e.g., sections of appropriately sized tubing, and the like, may be received and/or otherwise attached, similar to the airway device 110 of FIGS. 3A and 3B. In this alternative, the lumens 250, 260 may be attached to the clam-shell components 210a, 210b by one or more of an interference fit within the recesses, one or more cooperating connectors (not shown), bonding with adhesive, sonic or thermal welding or fusing, and the like.

In another embodiment, an outer shell (not shown) may be created to provide the proximal and distal portions 20, 30 of the airway device 10, and an insert (also not shown) may be positioned within and/or otherwise attached to the outer shell that includes a central instrument passage therethrough. Recesses in the walls of the outer shell and/or insert may together provide additional lumens, e.g., a sampling and fluid delivery lumen, that are substantially isolated from the instrument passage (other than at one or more communication ports).

Turning to FIGS. 2A-2C, an exemplary method will now be described for using an airway device 10' (which may be any of the embodiments herein), e.g., to introduce an endoscope or other device into a patient's body via the patient's oral cavity, to perform a medical procedure. Initially, the distal portion 30' of the airway device 10' may be introduced into the patient's oral cavity towards the pharyngeal region (not shown), e.g., until the proximal end 22' of the proximal portion 20' is located adjacent the patient's mouth, for example, until the proximal portion 22' at least partially enters the oral cavity and/or the flange 40' on the proximal end 22' is disposed adjacent the patient's teeth (not shown). Optionally, if the airway device 10 includes a transition portion 26 between the proximal and distal portions 20, 30 having a "U" shaped cross-section including lower edges 27a, similar to the airway device 10 of FIGS. 1A-1G, when the distal portion 30 of the airway device 10 is introduced into the oral cavity, the lower edges 27a may be positioned adjacent the patient's tongue to substantially stabilize the tongue.

As shown in FIG. 2C, a distal end 94 of an instrument, e.g., endoscope 90, may be introduced through the enclosed passage 23' in the proximal portion 20' and into the channel 32' of the distal portion 30,' e.g., to introduce the distal end 94 of the endoscope into the pharyngeal region (not shown). As best seen in FIG. 2B, the distal tip 34' of the airway device 10' may include a recess 34a' therein. As the distal end 94 of the endoscope 90 is advanced into the channel 32,' the distal end 94 may be directed along the channel 32' and through the recess 34a' such that the distal end 94 curves along a greater radius of curvature 95 than the radius of curvature 37' of the distal portion 30' of the airway device 10.' Because the bottom or inside of the channel 32' is open, a region of the endoscope 90 proximal to the distal end 94 may move away from the wall of the channel 32' rather than being forced into a tighter bend. Such a tighter bend, e.g., within a fully enclosed passage may increase frictional resistance of the endoscope 90 to further advancement, and therefore the open channel 32' may allow the endoscope 90 to be advanced more easily.

Once the distal end 94 is located within the pharyngeal region beyond the distal tip 34,' the endoscope 90 may be advanced into a desired body region, e.g., the esophagus, stomach, lungs, or other region or cavity within the patient's body, where a procedure may be performed. Optionally, with reference to the airway device of FIGS. 1A-1G, during the procedure, one or more fluids, e.g., oxygen, may be delivered via the fluid delivery lumen 60, e.g., into the pharyngeal region or otherwise adjacent the distal portion 303. For example, with the outlet 64 located adjacent the distal tip 34, oxygen may be delivered directly into or immediately adjacent the trachea, which may enhance delivery into the lungs. In addition or alternatively, fluids may be aspirated into the fluid delivery lumen 60, if desired, or the airway device may include a separate aspiration lumen (not shown), which may be used to aspirate secretions or other materials within the pharyngeal region adjacent the distal portion 30.

In addition or alternatively, one or more gas concentrations of respiratory air of the patient may be monitored via the inlet port 54 in the airway device 10. In the embodiment shown in FIGS. 1A-1G, the inlet port 54 may be located closer to the proximal end 22 of the airway device 10 than the outlet port 64 of the fluid delivery lumen 60, e.g., to reduce false concentration readings from the inlet port 54 due to exposure to the fluid delivered via the outlet port 64, as described elsewhere herein.

Once the procedure is complete, with reference again to FIG. 2C, the endoscope 90 and/or any other instruments introduced using the airway device 10' may be withdrawn through the airway device 10.' The airway device 10' itself may then be removed from the oral cavity.

Optionally, any of the embodiments herein may include one or more of additional features or variations, such as those described further below. For example, turning to FIGS. 5A and 5B, alternative embodiments of airway devices 310a, 310b are shown that may generally be constructed similar to other embodiments herein, e.g., including a proximal portion (not visible), a distal portion 330a, 330b, a flange 340a, 340b, and an instrument passage 312a, 312b extending between the proximal and distal portions. Unlike previous embodiments, at least a portion of the instrument passages 312a, 312b may include a configuration to facilitate introduction of an endoscope of other device (not shown) and/or facilitate respiration, aspiration, or other actions.

Figure 5A:
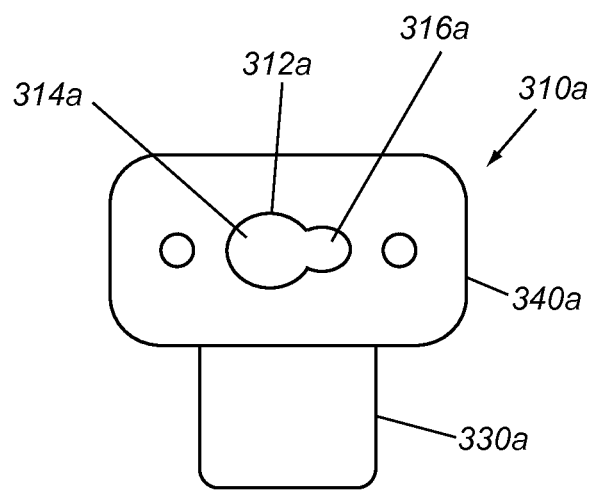
FIGS. 5A and 5B are end views of alternate embodiments of an airway device including an instrument passage that includes a special cross-section or configuration.

For example, in FIG. 5A, at least a proximal region of the instrument passage 312a includes an asymmetrical cross-section, e.g., including a relatively large region 314a and a relatively small region 316a disposed adjacent one another. In the embodiment shown, both regions 314a, 316a may be substantially circular or elliptical and are overlapped slightly such that the perimeter of each region is more than half of a circle. The large region 314a may have a diameter or other cross-section and least somewhat larger than an endoscope or other device (not shown) intended to be introduced through the instrument passage 312a. For example, the larger region 314a may be sized and shaped to slidably receive an endoscope therein, thereby providing a guide for introducing the endoscope into the airway device 310a with minimal lateral movement.

Because the sliding fit may reduce or substantially eliminate the ability of air to flow around the endoscope through the large region 314a, the small region 316a provides an airway passage through which air may pass freely, e.g., even with an endoscope introduced into the large region 314a. In addition, the small region 316a may accommodate introducing another instrument into the instrument passage 312a adjacent to the endoscope. For example, an aspiration tube or other device may be introduced into the small region 316a, e.g., to aspirate material adjacent the distal portion 330a of the airway device 310a.

In one embodiment, both the large and small regions 314a, 316a may extend from the flange 340a, through the proximal portion into the distal portion 330a. Alternatively, one or both of the regions 314a, 316a may extend only through the flange 340a or through the proximal portion, and may then terminate at a C" shaped channel or a larger single, enclosed passage extending through the distal portion 330a.

Figure 5B:
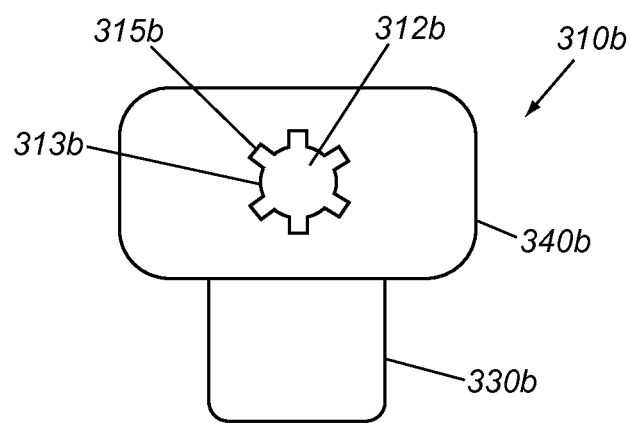

Similarly, the airway device 310b of FIG. 5B includes an instrument passage 312b that may slidably receive an endoscope or other device, yet accommodate flow of air around the endoscope. As shown, the instrument passage 312b includes a central, circular or elliptical region 313b sized to slidably receive an endoscope or other device (not shown), and a plurality of channels 315b surrounding the central region 313b. Thus, the endoscope may slide along ribs of the central region 313b between the channels 315b, yet allow air to flow easily through the channels 315b. Similar to the previous embodiment, the central region 313b and channels 315b may extend from the flange 340b through the proximal portion into the distal portion 330b, or may terminate at a "C" shaped channel or other larger passage through the distal portion 330b.

Figure 6A:
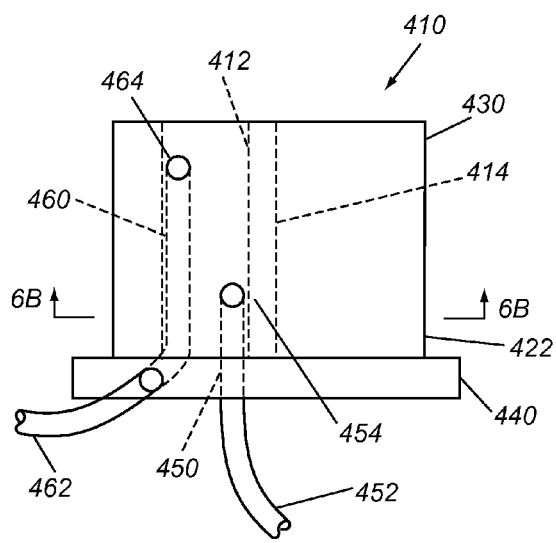
FIG. 6A is a top view of another embodiment of an airway device including an instrument passage and an airway passage disposed adjacent one another.
Figure 6B:
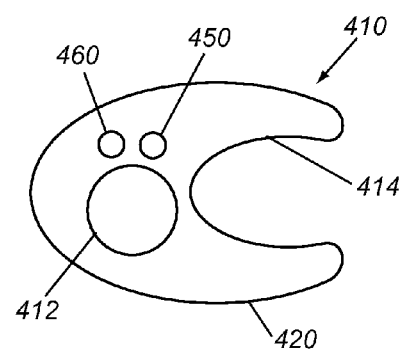
FIG. 6B is a cross-sectional view of the airway device of FIG. 6A, taken along line 6B-6B.

Turning to FIGS. 6A and 6B, another embodiment of an airway device 410 is shown that includes a substantially straight proximal portion 420 and a curved distal portion 430 (the curvature not being shown for simplicity). Generally, similar to other embodiments herein, the airway device 410 includes an instrument passage 412, a sampling lumen 450, and a fluid delivery lumen 460, extending distally from a proximal end of the airway device 410, e.g., from ports in the flange 440. Unlike the previous embodiments, the airway device 410 includes an airway passage 414 that extends between the proximal and distal portions 420, 430, e.g., substantially isolated and/or separate from the instrument passage 412. As best seen in FIG. 6B, in this embodiment, the airway passage 414 is a longitudinal channel extending between the proximal and distal portions 420, 430 that is open laterally, e.g., on the side opposite the instrument passage 412.

Figure 6C:
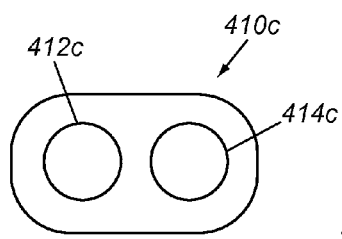
FIGS. 6C-6E are alternative cross-sections that may be provided for the airway device of FIG. 6A.

In alternative embodiments, however, the airway passage 414 and/or instrument passage 412 may have other cross-sections or configurations. For example, as shown in FIG. 6C, both the instrument passage 412c and the airway passage 414c are fully enclosed. In this embodiment, the passages 412c, 414c may be substantially circular as shown, or may have similar cross-sections to one or more devices intended to be introduced therethrough, similar to other embodiments herein. Thus, the passages 412c, 414d may have similar sizes and/or cross-sections to one another, or may have different sizes and/or cross-sections, as desired.

Figure 6D:
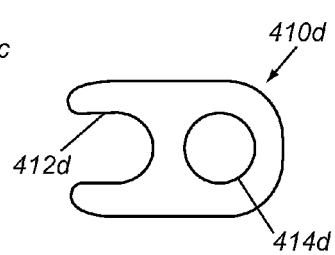
Figure 6E:
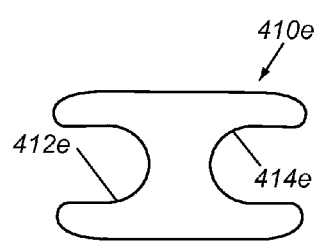

Alternatively, as shown in FIG. 6D, the instrument passage 412d may be a longitudinal channel that is open laterally, and the airway passage 414d is fully enclosed. In yet another alternative, shown in FIG. 6E, both the instrument passage 412e and the airway passage 414e are longitudinal channels that are open laterally, e.g., in opposite directions away from one another. It will also be appreciated that, in any of these embodiments, the instrument and airway passages 412 414 may extend from the flange 410 through the proximal portion into the distal portion 430, or the passages 412, 414 may end at the proximal portion and communicate with a "C" shaped channel or other single or multiple passages (not shown) extending along the distal portion 430.

Thus, with reference to FIGS. 6A and 6B (although also applicable to the alternative embodiments) if an endoscope or other device (not shown) is directed into the instrument passage 412 with a sliding fit that prevents substantial air flow around the endoscope, the airway passage 414 may allow air to freely pass therethrough, e.g., allowing substantially normal respiration by the patient.

As best seen in FIG. 6A, the sampling lumen 450 may communicate between a connector port 452 and an inlet port 454, e.g., located within the instrument passage 412 within the proximal portion 420, and the fluid delivery lumen 460 may communicate between a connector port 462 and outlet port 464, e.g., located within the instrument passage 412 within the distal portion 430. Alternatively, one or both of the inlet port 454 and the outlet port 464 may be located within the airway passage 414 instead of the instrument passage 412. For example, it may be desirable to place the inlet port 454 within the airway passage 414 if the instrument passage 412 has a size only slightly larger than an endoscope or other device introduced therethrough such that air flow around the device is unlikely.

Turning to FIGS. 7A-7D, another embodiment of an airway device 510 is shown that includes a substantially straight, enclosed proximal portion 520, a curved distal portion 530 including a "C" shaped wall, and an instrument passage 512 extending therebetween, similar to other embodiments herein. Also similar to other embodiments herein, the airway device 520 includes a flange 540 on a proximal end 522 of the proximal portion 520, and sampling and fluid delivery lumens 550, 560.

Unlike previous embodiments, a valve 570 is provided within the instrument passage 512, e.g., within the enclosed passage 523 within the proximal portion 520, e.g., within or immediately adjacent the flange 540. The valve 570 may be biased to close, e.g., to substantially seal the instrument passage 523, yet resiliently open to accommodate receiving an endoscope or other instrument (not shown) therethrough into the instrument passage 512. For example, the valve 570 may be a resiliently expandable valve, e.g., formed from silicone or other elastomeric or resilient material. Alternatively, the valve 570 may be a flap valve, and the like that may hinge, fold, or otherwise bend inwardly to accommodate introduction of an endoscope into the instrument passage 512, yet automatically close again when the endoscope is removed.

Figure 7C:
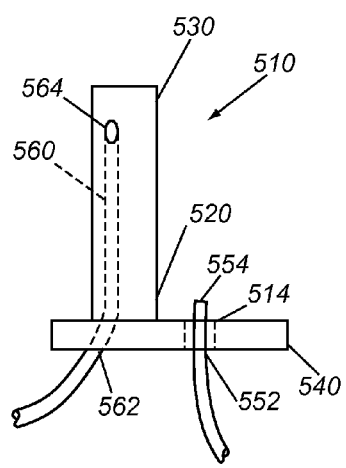
Figure 7D:
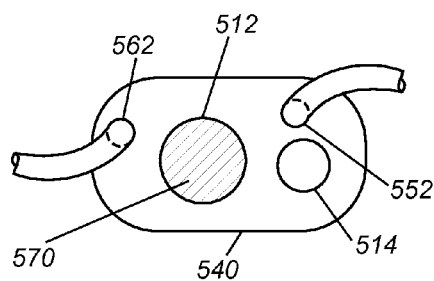

In addition, unlike previous embodiments, the airway device 510 includes an airway passage 514 adjacent the instrument passage 512 that extends through the flange 540. As best seen in FIGS. 7A and 7C, the airway passage 514 may simply be an opening through the flange 540 that does not communicate with the proximal or distal portions 520, 530 of the airway device 510. Thus, in this embodiment, the proximal and/or distal portions 520, 530 of the airway device 510 may have a narrower width than the oral cavity within which the airway device 510 is introduced, e.g., to accommodate respiration gases passing around the proximal and/or distal portions 520, 530 and through the airway passage 514.

In this embodiment, the fluid delivery lumen 560 may communicate with an outlet port 464 in the instrument passage 512, e.g., within the distal portion 530, while the sampling lumen 550 may communicate with an inlet port 454 disposed adjacent the airway passage 514. Thus, respiration gases sampled using the sampling lumen 550 may be at least somewhat isolated and/or remote from the fluids, e.g., oxygen, delivered through the outlet port 564 within the instrument passage 512. This may result in more accurate carbon dioxide, pressure, or other readings using the sampling lumen 550, as described elsewhere herein.

In addition, the valve 570 may provide a more positive pressure environment for oxygen or other gas or fluid delivered into the instrument passage 512. For example, without an endoscope in the instrument passage 512, the valve 570 may remain closed, substantially sealing the instrument passage 512 from the outside environment, which may enhance delivery of oxygen into the patient's trachea and lungs. In addition, with the valve 570 closed, the instrument passage 512 may provide a reservoir for storing oxygen or other gas delivered via the fluid delivery lumen 560. This may also enhance delivery of oxygen into the lungs and/or may provide a generally positive pressure environment within the oral cavity and/or pharyngeal region. Alternatively, it will be appreciated that a similar valve may be provided in the instrument passage (and/or the airway passage) of any of the embodiments herein. Alternatively, the valve 570 may function substantially uni-directionally, e.g. providing little resistance to air inflow during inspiration, but providing at least a partial seal resisting flow during exhalation. Further alternatively, the valve 570 may open in either direction under relatively little pressure or vacuum, but may prevent substantial flow under very low pressure, e.g. to decrease passive escape of delivered oxygen from the oropharynx.

Alternatively, in any of the embodiments herein, the distal portion of the airway device may be configured to create an oxygen reservoir in situ, e.g., within the pharyngeal region. For example, the size and/or shape of the distal portion may dilate or hold open tissues surrounding the pharyngeal region, which may increase the volume of the space adjacent the distal end of the airway device. Thus, oxygen delivered via the fluid delivery lumen into this space may be stored under positive pressure until inhaled by the patient.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented methods and/or processes as a particular sequence of steps. However, to the extent that the methods do not rely on the particular order of steps set forth herein, the methods should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An airway device for introducing an endoscope or other device into a patient's gastrointestinal system or other body region via the patient's oral cavity, comprising:
    a tubular proximal portion sized for placement in an oral cavity and comprising first and second side walls opposite one another and upper and lower surfaces extending between the side walls to enclose a passage for receiving an endoscope therethrough and defining a central axis of the proximal portion;
    a curved distal portion extending from the proximal portion, the distal portion comprising a "C" shaped wall defining a channel extending from the passage in the proximal portion to a distal tip of the distal portion, and wherein the distal tip comprises a curved recess between rounded distal tabs;
    a flange extending radially outwardly from a proximal end of the proximal portion for placement adjacent the patient's teeth when the airway device is inserted into the patient's oral cavity; and
    a sampling lumen extending at least partially along the proximal portion and comprising a connector port on a face of the flange for coupling to tubing from a respiratory monitoring device and an inlet port located on the first side wall of the proximal portion thereby communicating with the passage.

2. The airway device of claim 1, wherein the proximal portion has a length along the central axis extending through the passage that is shorter than a length of the distal portion along the central axis.

3. The airway device of claim 1, further comprising a "U" shaped transition portion extending between the proximal and distal portions to define a length and having a curved wall defining a substantially uniform cross-sectional arc along the entire length and lower edges extending substantially parallel to the central axis along the entire length, and wherein the wall of the distal portion defines a cross-sectional arc that is smaller than the cross-sectional arc defined by the wall of the transition portion.

4. The airway device of claim 3, wherein the proximal portion, the transition portion, and the distal portion are integrally molded together as a single part.

5. An airway device for introducing an instrument into a patient's body via the patient's oral cavity, comprising:
    a tubular proximal portion sized for placement in an oral cavity comprising an enclosed passage extending from a proximal end thereof for receiving an instrument therethrough and defining a central longitudinal axis;
    an arcuate transition portion extending from the proximal portion along a length extending substantially parallel to the central axis and comprising an upper wall and opposite side walls extending along the length defining a partially enclosed passage including an open bottom extending along the length communicating with the enclosed passage such that the transition portion defines a substantially uniform cross-sectional arc along the length and includes lower edges that extend along the length of the side walls substantially parallel to the central axis; and a curved distal portion extending distally from the transition portion to a distal end, the distal portion comprising a "C" shaped wall defining a channel communicating with the partially enclosed passage and extending to the distal end, the wall of the distal portion defining an arc that is smaller than a periphery of the transition portion, and wherein the distal end terminates in a distal tip comprising a curved recess between rounded distal tabs.

6. The airway device of claim 5, wherein the lower edges of the transition portion are spaced apart from one another by a predetermined distance and have sufficient length to extend through the majority of the oral cavity.

7. The airway device of claim 5, wherein the lower edges of the transition portion are located further from the central axis than a lower wall of the proximal portion.

8. The airway device of claim 5, wherein the lower edges of the transition portion extend substantially parallel to a lower wall of the proximal portion.

9. The airway device of claim 5, further comprising a flange extending outwardly from the proximal end for placement adjacent the patient's teeth when the airway device is inserted into the patient's oral cavity.

10. The airway device of claim 1, further comprising a fluid delivery lumen extending at least partially along the proximal portion and comprising a connector port on the face of the flange for coupling to a fluid source and an outlet port communicating with the passage.

11. The airway device of claim 10, wherein the fluid delivery sampling lumen is located on the first side wall of the proximal portion adjacent the sampling lumen.

12. The airway device of claim 1, wherein the sampling lumen and inlet port are integrally formed in the first side wall of the proximal portion.

13. The airway device of claim 3, wherein the lower surface of the proximal portion comprises a concave edge adjacent an open bottom of the transition portion.

14. The airway device of claim 5, wherein the proximal portion comprises a lower surface including a concave edge adjacent the open bottom of the transition portion.

15. An airway device for introducing an endoscope or other device into a patient's gastrointestinal system or other body region via the patient's oral cavity, comprising:
a tubular proximal portion sized for placement in an oral cavity and comprising first and second side walls opposite one another and upper and lower surfaces extending between the side walls to enclose a passage for receiving an endoscope therethrough defining a central axis of the proximal portion;
a curved distal portion extending from the proximal portion, the distal portion comprising a "C" shaped wall defining a channel extending from the passage in the proximal portion to a distal tip of the distal portion, a flange extending radially outwardly from a proximal end of the proximal portion for placement adjacent the patient's teeth when the airway device is inserted into the patient's oral cavity, a sampling lumen extending at least partially along the proximal portion and comprising a connector port on a face of the flange for coupling to tubing from a respiratory monitoring device and an inlet port located on the first side wall of the proximal portion thereby communicating with the passage, and
wherein the distal tip comprises a curved recess between rounded distal tabs, and the lower surface of the proximal portion comprises a distal edge having a concave shape, the curved recess and concave shape of the distal edge configured to slidably engage a cylindrical instrument introduced through the passage.

* * * * *